US012714880B2

(12) United States Patent
Gooding et al.

(10) Patent No.: US 12,714,880 B2
(45) Date of Patent: Aug. 25, 2026

(54) METHOD FOR QUANTIFYING PATIENT SET UP ERRORS IN RADIOTHERAPY

(71) Applicant: Boston Scientific Scimed, Inc., Maple Grove, MN (US)

(72) Inventors: Mark Gooding, Oxfordshire (GB); John Sage, Maple Grove, MN (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 109 days.

(21) Appl. No.: 18/854,093

(22) PCT Filed: Apr. 26, 2023

(86) PCT No.: PCT/EP2023/061007
§ 371 (c)(1),
(2) Date: Oct. 4, 2024

(87) PCT Pub. No.: WO2023/213655
PCT Pub. Date: Nov. 9, 2023

(65) Prior Publication Data

US 2025/0339711 A1 Nov. 6, 2025

(30) Foreign Application Priority Data

May 3, 2022 (GB) ..................................... 2206425

(51) Int. Cl.
*A61N 5/00* (2006.01)
*A61N 5/10* (2006.01)
(Continued)

(52) U.S. Cl.
CPC ......... *A61N 5/1038* (2013.01); *A61N 5/1037* (2013.01); *A61N 5/1049* (2013.01);
(Continued)

(58) Field of Classification Search
CPC .... A61N 2005/1052; A61N 2005/1055; A61N 2005/1061; A61N 2005/1074;
(Continued)

(56) References Cited

U.S. PATENT DOCUMENTS 12,303,714 B2 * 5/2025 Finnson ................ G16H 20/40
2019/0314644 A1 10/2019 Chen et al.
(Continued)

FOREIGN PATENT DOCUMENTS

JP 201889065 A 6/2018
WO 2015085252 A1 6/2015

OTHER PUBLICATIONS

Mittauer Kathryn et al.: "A New Era of Image Guidance with Magnetic Resonance-guided Radiation Therapy for Abdominal and Thoracic Malignancies", CUREUS, Apr. 4, 2018 (Apr. 4, 2018), US, XP093062925, ISSN: 2168-8184, DOI: 10.7759/cureus.2422.
(Continued)

*Primary Examiner* — Dani Fox
(74) *Attorney, Agent, or Firm* — Seager, Tufte & Wickhem, LLP

(57) ABSTRACT

A method and system for determining changes between a planning image and a treatment image of a subject is described. The method comprising the steps of: defining one of more clinical volumes on the planning image of a subject and defining a planning envelope volume around the clinical volume for the planning image; acquiring a treatment image from the subject for a location corresponding to the location of the planning image; wherein the treatment image will have the same planning envelope volume as the planning image; determining the location of the one or more clinical volumes on the treatment image relative to the planning envelope volume; determining an encapsulation metric for one or more of the clinical volumes defining the extent of
(Continued)

encapsulation of the clinical volume on the treatment image within the planning envelope volume on the treatment image.

20 Claims, 14 Drawing Sheets

(51) Int. Cl.
*G06T 7/00* (2017.01)
*G06T 7/149* (2017.01)

(52) U.S. Cl.
CPC ........... *G06T 7/0012* (2013.01); *G06T 7/149* (2017.01); *A61N 2005/1052* (2013.01); *A61N 2005/1055* (2013.01); *A61N 2005/1074* (2013.01)

(58) Field of Classification Search
CPC .... A61N 5/103; A61N 5/1037; A61N 5/1038; A61N 5/1049; G06T 7/0012; G06T 7/149
See application file for complete search history.

(56) References Cited

U.S. PATENT DOCUMENTS

| | | | |
|---|---|---|---|
| 2020/0061389 | A1 | 2/2020 | Willcut et al. |
| 2021/0322789 | A1 | 10/2021 | Zankowski et al. |
| 2021/0402215 | A1 | 12/2021 | Morgas et al. |

OTHER PUBLICATIONS

Brouwer et al., “Identifying Patients who May Benefit from Adaptive Radiotherapy: Does the Literature on Anatomic and Dosimetric Changes in Head and Neck Organs at Risk during Radiotherapy Provide Information to Help?” Radiotherapy and Oncology, vol. 115, pp. 285-294. Available online Jun. 17, 2015.

Fiorino et al., “Introducing the Jacobian-Volume-Histogram of Deforming Organs: Application to Parotid Shrinkage Evaluation,” Physics in Medicine & Biology, vol. 56, pp. 3301-3312. May 10, 2011.

Hargrave et al., “A Feature Alignment Score for Online Cone-Beam CT-Based Image Guided Radiotherapy for Prostate Cancer,” Medical Physics, vol. 45, No. 7, pp. 2898-2911. Jul. 2018.

ICRU Report 50: Prescribing, Recording and Reporting Photon Beam Therapy: Journal of the ICRU, vol. 26, No. 1, 3 Pages. Sep. 1993.

Low et al., “A Technique for the Quantitative Evaluation of Dose Distributions,” Medical Physics, vol. 25, pp. 656-661. Accepted for Publication Mar. 2, 1998.

Schaly et al., “Alert System for Monitoring Changes in Patient Anatomy during Radiation Therapy of Head and Neck Cancer,” Journal of Applied Clinical Medical Physics, vol. 22, pp. 168-174, Accepted Jun. 5, 2021.

Wang et al., “Adaptive Radiotherapy Based on Statistical Process Control for Oropharyngeal Cancer,” Journal of Applied Clinical Medical Physics, vol. 21, No. 9, pp. 171-177. Jul. 12, 2020.

ICRU Report 62: Prescribing, Recording and Reporting Photon Beam Therapy (Supplement to ICRU Report 50): Journal of the ICRU, vol. 32, Issue 1, Nov. 1999.

Borgefors, “On Digital Distance Transforms in Three Dimensions,” Computer Vision and Image Understanding, vol. 64, Issue 3, pp. 368-376. Nov. 1996.

https://viewray.com/mri-guided-smart Military University Hospital Prague Selects ViewRays MRIdian® MRI-Guided Radiation Therapy to Treat Cancer Patients, 2 Pages. Mar. 7, 2023.

* cited by examiner 601
602
603
604
605
606
607
B
A
-15 to -10mm
-10 to -5mm
-5 to 0mm
0 to 5mm
5 to 10mm
10 to 15mm
15 to 20mm
20 to 25mm
25 to 30mm 608
609
611
610
A
15 to 10mm
10 to 5mm
5 to 0mm
0 to -5mm
-5 to -10mm
-10 to -15mm
-15 to -20mm
-20 to -25mm
-25 to -30mm

METHOD FOR QUANTIFYING PATIENT SET UP ERRORS IN RADIOTHERAPY

CROSS-REFERENCE TO RELATED APPLICATIONS

This application is a national stage application filed under 35 U.S.C. § 371 and claims priority to Patent Cooperation Treaty (PCT) Application No. EP2023/061007, filed Apr. 26, 2023 and titled "A Method For Quantifying Patient Set Up Errors In Radiotherapy," which application claims priority to Great Britain (GB) Patent Application No. 2206425.7, filed May 3, 2022, the disclosures of which are both incorporated herein by reference in their entirety.

FIELD OF INVENTION

This invention relates to the fields of medical imaging and medical image processing, in particular to identifying changes in medical images dues to changes in patient anatomical position as the scan is acquired, and in particular in the field of radiotherapy treatment.

BACKGROUND OF INVENTION

During radiotherapy a patient has a planning medical image acquired, most commonly Computed Tomography (CT) but increasingly this may be Magnetic Resonance (MR). From this medical image, a plan is produced which is used for a number of radiotherapy treatment sessions. These treatment sessions are known as fractions. One of the issues with this approach is that the planning image is not an exact representation of the patient anatomy on each treatment session. There are random variations in where the patient anatomy will be on each session with respect to its appearance on the planning image. There are also systematic changes in patient anatomy that may occur with time due to weight loss, tumour shrinkage, or other such processes. Image Guided Radiotherapy (IGRT) and Adaptive Radiotherapy (ART) are techniques that use imaging over the course of treatment to monitor anatomical changes to optimise the patient position, in the case of IGRT, or to modify the treatment plan, in the case of ART.

To produce radiotherapy treatments which are robust to patient position variation, margins are applied to certain regions identified on the planning image. An oncologist will identify a Clinical Target Volume (CTV) as the region possibly containing disease to be treated with radiation. A margin will be applied to the CTV to create a Planning Target Volume (PTV). The PTV is the region which will have radiation applied to it to ensure the CTV receives the required radiation dose. The PTV is an envelope of space encapsulating all the likely positions of the CTV due to anatomical position variation. Similar definitions exist for sensitive healthy organs which are to be avoided. An Organ at Risk (OAR) has a margin applied to produce a Planning Risk Volume (PRV). These concepts were formalised in ICRU reports 50 and 62 [1,2]. Because this invention applies equally to both target areas and healthy areas we will group these definitions, with the CTV and OAR being grouped together as Clinical Volumes (CV) and the PTV and PRV being grouped together as Planning Envelope Volumes (PEV). PEVs are almost always explicitly defined during radiotherapy planning, by way of a contour drawn during the planning, but it is possible for them to be implicitly defined, such as CV plus a margin of 10 mm.

During IGRT and ART a key decision is whether the CV are still encapsulated by their respective PEV. A CTV that moves outside the PTV has an increased risk of being missed by the radiation treatment. Similarly, an OAR that moves outside a PRV has an increased risk of moving into the high dose region. If the CV extend outside the PEV then the assumptions of the original plan are invalid and either the patient position must be shifted to bring the CV back within the PEV or a new plan should be considered. In the scenario where the user wishes to perform a position correction then the majority of radiotherapy devices facilitate this with an automated linear movement of the patient couch. More advanced systems will allow for an automated correction of patient angles as well as linear shifts.

A flowchart for an example current process 100 for IGRT/ART is shown in FIG. 1. The process has two phases. A planning phase 101, occurs prior to the first radiotherapy treatment. At step 103 either a single or a multiplicity of Clinical Volumes, CVs, are identified on a planning 3D image, such as a CT scan. Some CVs will correlate exactly with organs visible in the scan, but others may not, such as a Clinical Target Volume identifying areas of risk of cancer disease. At step 104, PEV are produced around a single or multiplicity of CVs to account for potential movement of the CV during treatment. The number of PEVs may differ from the number of CVs, for example because PEVs are not produced for not every CV or because multiple CVs may be combined into a single PEV A radiation treatment plan is then produced in step 105, using the PEV of step 104 to optimise the dose delivered to treatment targets whilst keeping dose to organs at risk below set thresholds.

The treatment phase 102 will be performed once or for a multiplicity of treatment factions. Step 106 occurs for each treatment fraction, or selected treatment fractions, where an imaging system integrated into the treatment machine acquires an image prior to treatment delivery, typically this will be acquired up to 15 minutes before the start of the treatment, although the patient would remain in the treatment position for this time. At step 107 a user visually compares this image to the planning image to verify that each critical CV of step 104 is still contained within the associated PEV. Typically this is done on a dedicated image review workstation which will allow for various different methods of image comparison. On the basis of this evaluation the user, in step 120, decides whether to proceed with the treatment, possibly with a correction to the patient position.

Within the prior art most IGRT and ART systems only provide tools for the manual, subjective assessment of whether a CV is contained within PEV. The few systems that do provided an automated assessment, designed for real-time assessment of patient anatomy, provide a Boolean yes/no indicator, for example showing green if the CV are within the PEV and red otherwise [3]. The problem with an indicator like this is that it gives no means to quantify a change and track the potential development of an issue over time.

Some systems have attempted to use quantitative measures to track changes over time. Wang et al [4] used Varian's Velocity "Adaptive Monitoring Navigator" to track changes in the volume of structures and any shifts in the structure centre position. These metrics are useful if the CV being tracked is rigid, but in modern radiotherapy some CV can be very complex and do not move simply. Tracking the movement of the centre of a CV may miss parts of the CV moving outside their PEV.

A survey of academic studies found many other papers which reported on frameworks and metrics for monitoring patient changes during radiotherapy. In particular, Brouwer et al [5] conducted a systematic review of papers on techniques for ART in head and neck cancer. The metrics of anatomical change they identified from 51 studies were weight, body thickness, CV volume, CV density, CV position, CV angle and variations on these, such as change, rate of change or changes occurring at a specific anatomical point. As above with complex CV these metrics could miss parts of the CV moving outside their PEV.

Several studies [6-8] reported more complex metrics of anatomical change based on the change of either the patient image directly or structures identified on them.

Schaly et al [6] investigated the gamma index difference between CT scans. Gamma index is a method developed for the comparison of two three-dimensional radiation dose distributions [9]. It is sensitive both to changes in voxel intensity and distance to agreement, that being the distance between a voxel in the reference image and a voxel of the same intensity in the test image. Gamma index will certainly be sensitive to changes in the position of the CV but as a global, image-based metric it does not explicitly measure the adequacy of the PEV in covering the CV; a poor gamma index score will be affected by anatomical changes anywhere in the image.

Fiorino et al [7] reported on the use of a Jacobian Volume Histogram to quantify changes to a deforming organ. In this method a deformable registration is applied between the reference image and the test image. The Jacobian matrix of the deformable vector field is then calculated and the values in the region of the CV are plotted in a histogram. This provides a measure of the expansion and contraction of voxels throughout the CV. This has the advantage over the method of Schaly that it is focused on a specific CV and not the whole volume. However, it does not directly address the issue of the adequacy of a PEV in encompassing an CV. Changes within an CV could occur which do not result in the CV extending beyond the PEV but result in a high Jacobian change.

Hargrave et al [8] reports an approach that is closest to the present invention. This measure uses the Hausdorff distance between the original CV and the CV during treatment as a metric. The Hausdorff distance is a measure of the worst-case difference between two sets of contours. This would spot a significant change in a complex CV but is not explicitly linked to the issue of clinical interest, whether the CV moves outside the PEV. A CV shrinking and moving further inside the PEV is not a clinical problem but would register as a change. This lack of directionality in the metric would make its use in tracking changes more difficult.

[1] ICRU Report 50: Prescribing, Recording and Reporting Photon Beam Therapy: Journal of the ICRU, Volume 26 Issue 1, September 1993

[2] ICRU Report 62: Prescribing, Recording and Reporting Photon Beam Therapy (Supplement to ICRU Report 50): Journal of the ICRU, Volume 32 Issue 1, November 1999

[3] https://viewray.com/mri-guided-smart/

[4] Wang et al, Adaptive radiotherapy based on statistical process control for oropharyngeal cancer: J Appl Clin Med Phys 2020; 21:9:171-177

[5] Brouwer et al. Identifying patients who may benefit from adaptive radiotherapy: Does the literature on anatomic and dosimetric changes in head and neck organs at risk during radiotherapy provide information to help? Radiotherapy and Oncology 115 (2015) 285-294

[6] Schaly et al, Alert system for monitoring changes in patient anatomy during radiation therapy of head and neck cancer. J Appl Clin Med Phys. 2021; 22:168-174.

[7] Fiorino et al. Introducing the Jacobian-volume-histogram of deforming organs: application to parotid shrinkage evaluation, Phys. Med. Biol. 56 (2011) 3301-3312

[8] Hargrave et al. A feature alignment score for online cone-beam CT-based image-guided radiotherapy for prostate cancer. Med Phys. 45 (7), July 2018 2898-2911

[9] Low et al, A technique for the quantitative evaluation of dose distributions. Med Phys. 1998; 25:656-661.

Thus, the following problem(s) has (have) been resolved, by the present invention There is a need for simple, quantifiable metrics which easily relate changes between images acquired over a time period to assist in identifying changes in the anatomical position of a patient. Preferably, this information can used for treatment planning, in the presence of patient geometric changes and for these to be presented to a clinical user in a meaningful manner.

According to the invention there is provided a method for determining changes between a planning image and a treatment image of a subject, comprising the steps of: defining one of more clinical volumes on the planning image of a subject and defining a planning envelope volume around the clinical volume for the planning image; acquiring a treatment image from the subject for a location corresponding to the location of the planning image; wherein the treatment image will have the same planning envelope volume as the planning image; determining the location of the one or more clinical volumes on the treatment image relative to the planning envelope volume; determining an encapsulation metric for one or more of the clinical volumes defining the extent of encapsulation of the clinical volume on the treatment image within the planning envelope volume on the treatment image.

In an embodiment of the invention determining the encapsulation metric comprises the following steps: designating one or more representative points on the surface of the clinical volume; determining the shortest distance for the one or more representative points of the clinical volume to the planning envelope volume; wherein when the representative point on the clinical volume is within the Planning Envelope Volume, the shortest distance is classified as either a positive or negative internal distance, whereas when the representative point on the Clinical Volume is external to the Planning envelope Volume the shortest distance is an external distance classified with an opposite sign to the internal distance; and the encapsulation metric value is determined as either: the minimum of the signed shortest distance value when the internal distance is classified as positive, or the maximum of the signed shorted distance when the internal distance is classified as negative, of the distances for the one or more representative points.

In a preferred embodiment of the invention the planning image and treatment images are 3D images. Further preferably, the planning image and treatment image are CT, PET, SPECT or MRI images.

In a preferred embodiment of the invention after the planning envelope volume has been defined, a distance transform is calculated around the planning envelope volume and this is used to determine the encapsulation metric.

Further preferably the encapsulation metric is determined by simulation of translations of the one or more treatment clinical volumes relative to the planning envelope volume. In an embodiment of the invention the simulated translation is a linear translation.

In a preferred embodiment of the invention determining the location of the one or more clinical volumes on the treatment image relative to the planning envelope volume comprises one or more of: determining a geometric relationship between the planning image and the treatment image and mapping the clinical volume location across to the treatment image; identifying anatomical features on the treatment image to locate the clinical volume.

Preferably, the planning envelope volume is defined as the clinical volume plus a margin specified by a predetermined protocol.

In an embodiment of the invention, the clinical volume is a clinical target volume for treatment planning or gross tumour volume. In an alternative embodiment of this invention the clinical volume represents an organ at risk to be avoided in treatment.

In a preferred embodiment, the steps are repeated over a set time period to monitor changes in the encapsulation metric on the treatment images. Preferably, the set time period varies between 6 hours to 3 months.

In an embodiment of the invention the changes in the encapsulation metric with time are displayed to a user, In a preferred embodiment of the invention the subject is in a specified position in a scanner for the planning image and the treatment image, and the system user can adjust the subject position according to the one or determined encapsulation metrics.

Preferably, changes in the encapsulation metric with time are displayed to a user, wherein the display further shows when the encapsulation metric has exceeded a pre-set threshold indicating unsafe movement of the subject in the scanner.

Preferably, the method further comprising the step of displaying the one or more determined encapsulation metrics to a system user.

In a preferred embodiment, the method further comprising the step of using the encapsulation metric to determine a 3D representation showing a movement margin that illustrates how a subject can be moved within a scanner whilst maintaining or improving the position of the clinical volume relative to the position of the planning envelope volume.

Preferably, the clinical volume is displayed as a 3D rendered surface with the encapsulation metric for the surface indicated as a heat map on the surface.

In a further embodiment of the invention there is also provided a system for analysing medical images to determine changes between a planning image and a treatment image of a subject comprising: a processor configured to: determine one or more clinical volumes on a planning image of a subject, and defining a planning envelope volume around the clinical volume for the planning image; analyse a treatment image from the subject for a location corresponding to the location of the planning image; wherein the treatment image will have the same planning envelope volume as the planning image; determine the location of the one or more clinical volumes on the treatment image relative to the planning envelope volume; determine an encapsulation metric for one or more of the clinical volumes defining the extent of encapsulation of the clinical volume on the treatment image within the planning envelope volume on the treatment image.

Preferably, the processor is further configured to perform any of the method steps as described above.

In a preferred embodiment of the invention, the system further comprises a display to display at least one of: the planning image, the treatment image, the one or more clinical volumes, and the planning envelope volume.

In a further embodiment of the invention there is also provided a computer program product comprising instructions, which when the program is executed by a computer cause the computer to carry out the method steps as described above.

BRIEF DESCRIPTION OF THE DRAWINGS

Further details, aspects and embodiments of the invention will be described, by way of example only, with reference to the drawings. In the drawings, like reference numbers are used to identify like or functionally similar elements. Elements in the figures are illustrated for simplicity and clarity and have not necessarily been drawn to scale.

FIGS. 4(*b*) and (*c*) illustrate a clinical volume and a planning envelope volume on treatment images;

DETAILED DESCRIPTION

The invention is a system for monitoring and reporting changes between medical images acquired at different times. For example, they may be images acquired during radiotherapy treatment and planning. One possible application is to support IGRT (image guided radiotherapy) and ART (adaptive radiotherapy) decision making, but the invention is not constrained to this application. Other possible applications are deformable registration quality control, tracking disease progression or use in other image guided medical interventions where the movement of Clinical Volumes across sequential images is required.

Figure 10:
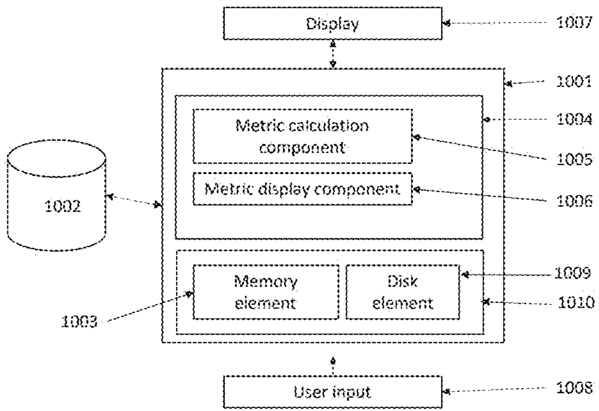
FIG. 10 is a simplified block diagram of a medical imaging system arranged to display medical images to a user.

FIG. 10 illustrates a simplified block diagram of an example of a medical imaging system 1000 arranged to enable medical images to be displayed to a user. In the illustrated example, the medical imaging system 1000 comprises one or more user terminals 1001, for example comprising a workstation or the like, arranged to access medical images stored within, for example, a database 1002 or other data storage apparatus. In the illustrated example, a single database 1002 is illustrated. However, it will be appreciated that the user terminal 1001 may be arranged to access medical images from more than one data storage apparatus. Furthermore, in the illustrated example the database 1002 is illustrated as being external to the user terminal 1001. However, it will be appreciated that the user terminal 1001 may equally be arranged to access medical images stored locally within a local storage module illustrated at 1010 on one or more internal storage elements, such as the memory element illustrated at 1003 or the disk element illustrated at 1009. The user terminal 1001 further comprises one or more signal processing modules, such as the signal processing module illustrated generally at 1004. The signal processing module(s) is/are arranged to executing computer program code, for example stored within local storage module 1009. In the illustrated example, the signal processing module(s) 1005 is/are arranged to execute computer program code comprising one or more of the patient change monitoring components(s) illustrates in the example as the metric calculation component 1005. The signal processing module 1004 in the illustrated example is further arranged to execute computer program code comprising one or more image display component(s) 1006; the image display component(s) 1006 being arranged to display in a meaningful manner any metrics of patient change such as those generated by the metric calculation component(s) 1005, to a user, for example on a display screen 1007 or the like. The medical imaging system 1000 may further comprise one or more user input devices, such as illustrated generally at 1008, to enable a user to interact with computer program code etc. executing on the signal processing module(s) 1004.

Figure 1:
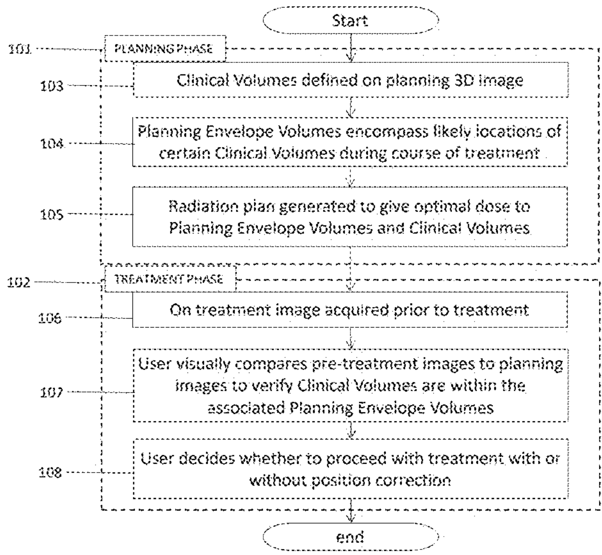
FIG. 1 shows a flowchart for a known process for Image Guided Radiotherapy/Adaptive radiotherapy.
Figure 2:
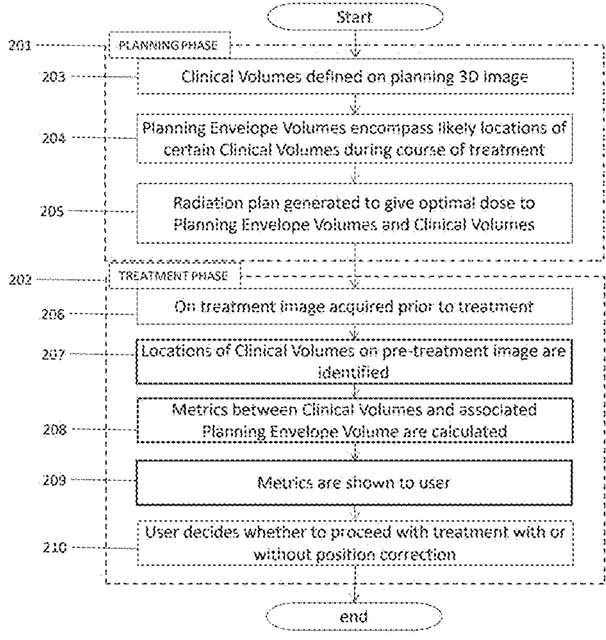
FIG. 2 shows a flowchart of the method according to a first embodiment of the invention.

In FIG. 2, the process shown in FIG. 1 is now shown incorporating the invention. As for FIG. 1, this process has two phases. A planning phase 201 that occurs prior to the first radiotherapy treatment, and a treatment phase 202. The treatment process is mostly unchanged. Items 201-206 and 210 all correspond with the identical items in FIG. 100. At step 203 of the planning phase either a single or a multiplicity of Clinical Volumes, are identified on a medical planning image of a subject. In an example of the invention the planning image and treatment images are 3D images. Preferably, the planning image and treatment image are CT, PET, SPECT or MRI images.

Some Clinical volumes will correlate exactly with organs visible in the scan, but others may not, such as a Clinical Target Volume identifying areas of risk of cancer disease. At step 204, planning envelope volumes are produced around a single or multiplicity of Clinical Volumes to account for potential movement of the Clinical Volume during treatment. The number of Planning envelope Volumes may differ from the number of Clinical Volumes, for example because Planning Envelope Volumes are not produced for not every Clinical Volume or because multiple Clinical Volumes may be combine into a single Planning Envelope Volume A radiation treatment plan is then produced in step 205, using the Planning Envelope Volume of step 204 to optimise the dose delivered to treatment targets whilst keeping dose to organs at risk below set thresholds.

The treatment phase 202 will be performed once or for a multiplicity of treatment factions. Step 206 occurs for each treatment fraction, or selected treatment fractions, where an imaging system integrated into the treatment machine acquires a treatment image prior to treatment delivery, typically this will be acquired up to 15 minutes before the start of the treatment, although the patient would remain in the treatment position for this time. Preferably, the treatment image for the subject is acquired for a location corresponding to the location of the planning image; such that the treatment image will have the same planning envelope volume as the planning image The invention supports the user evaluation of the images so that step 107 in FIG. 1 is replaced by steps 207-209 in FIG. 2. In step 207 the locations of the one or more Clinical Volumes on the treatment image are identified, preferably the location is determined relative to the location of the planning envelope volume. There are various ways to perform the task of step 207, the invention does not depend on a particular method and will work with any technically feasible method. For example, by determining the geometric relationship between the planning image and the treatment image and mapping the volume location across. Another method is by manually or automatically identifying the volumes from the anatomy on the treatment image to locate the clinical volume. In step 208, an encapsulation metric, detailed further below, is calculated between one or more Clinical Volumes on the treatment image and the associated Planning Envelope Volumes from the planning image. Preferably, the encapsulation metric for one or more of the clinical volumes defines the extent of encapsulation of the one or more clinical volumes on the treatment image within the planning envelope volume on the treatment image. This is shown to the user in step 209. This view might take a number of forms, incorporating any combination of the patient images, the Clinical Volumes and Planning Envelope Volumes, the metrics for this treatment session, the trend over previous sessions, a graphical representation of where problems have been detected, the metric values organised by surface angle or summary information in numerical or textual form. A number of these elements are demonstrated further in FIGS. 700, 800 and 900

Figure 3:
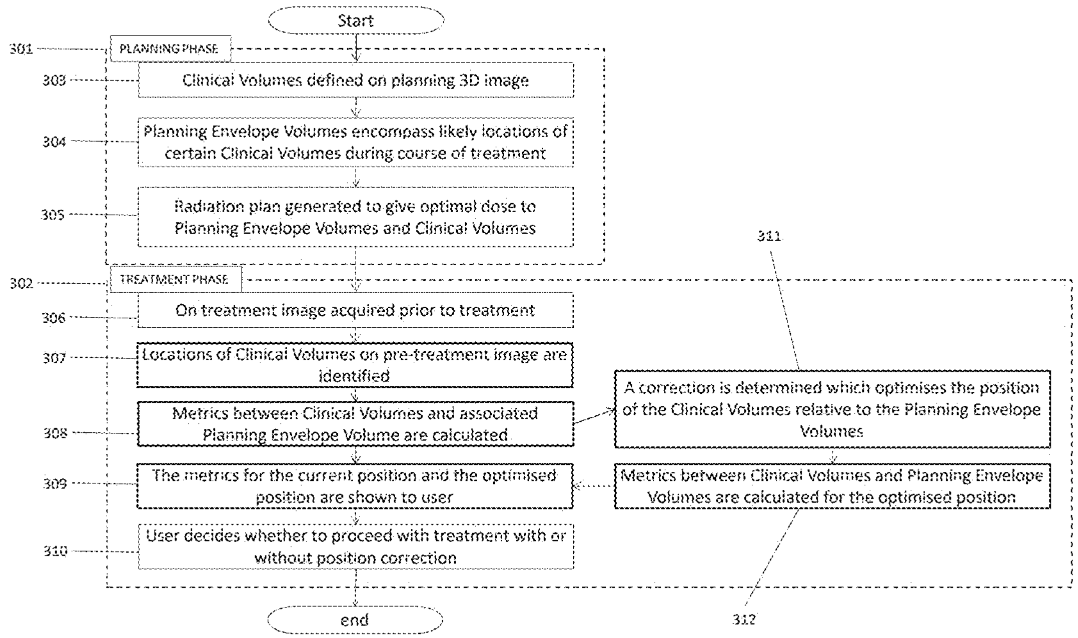
FIG. 3 shows a flowchart of the method according to a further embodiment of the invention.

A further example of the method of this invention is shown in FIG. 3. Items 301-306 and 320 all correspond to the identical items in FIG. 1. As in FIG. 2 the locations of the Clinical Volumes on the treatment image are determined in step 307 and an encapsulation metric is calculated between each of the treatment Clinical Volumes and the associated Planning Envelope Volumes in step 308. In step 309 a correction to the position of the treatment image is determined which best encapsulates the Clinical Volumes within the Planning Envelope Volumes and so minimises the encapsulation metric. Where there are multiple encapsulation metrics to be optimised any standard method to manage multiple objectives in an optimisation problem can be employed. For example, by setting priority rules by volume type or by weighting the separate metrics and summing to produce an overall score. In step 310 the individual encapsulation metrics for this optimised treatment position are calculated. In step 311 the encapsulation metrics for the original patient position are reported to the user alongside the potential encapsulation metric values if the optimal correction is performed.

Figure 4A:
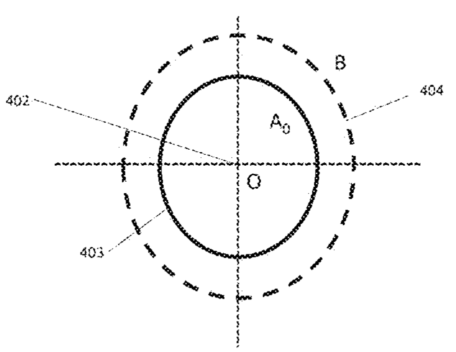
FIG. 4(*a*) illustrates a clinical volume and a planning envelope volume on a planning image.
Figure 4B:
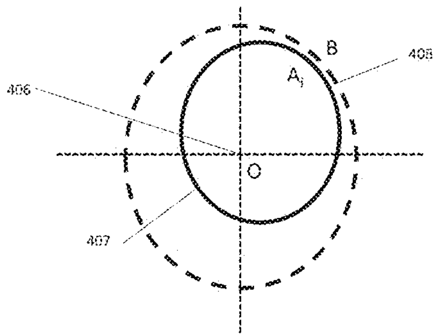
Figure 4C:
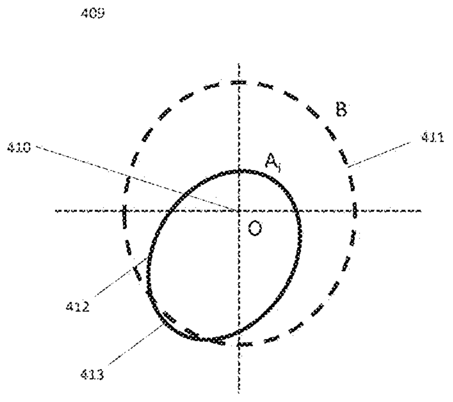

FIG. 400 demonstrates the concepts of the Clinical Volume and Planning Envelope Volume in the planning and treatment situations. FIG. 4(*a*) shows the situation in the planning image. We define a co-ordinate system with origin at O, item 402. The location of O is decided during the planning process, it can be any point on the treatment image, but typically corresponds to the isocentre of the radiotherapy treatment machine. The position of the Clinical Volume in the planning scan is shown as A0, item 403. The Planning Envelope Volume is shown entirely encompassing the Clinical Volume with a margin as B, item 404. FIG. 4(*b*) shows the situation at one of the treatment fractions, termed i. The period between treatment fractions typically varies between six hours and one week. Because the treatment is defined relative to the machine geometry the origin, item 406, and the position of the Planning Envelope Volume, item 408, are unchanged for each treatment fraction. However, the patient will generally not sit or lie within the machine geometry in exactly the same position as during the planning stage so the position of the Clinical Volume will change, as shown by Ai, item 407. In this example of the invention, the Clinical Volume has moved into the top right quadrant relative to the axes but still remains within the bounds of the Planning Envelope Volume. FIG. 4(*c*) shows the situation at a different one of the treatment fractions. Again the origin, item 410, and the Planning Envelope Volume, item 411, are unchanged. The Clinical Volume, item 412, in this example has not only moved relative to the Planning Envelope Volume but has also deformed compared to the original shape it had in the planning phase, item 403. The combination of movement and shape change has caused a portion of the Clinical Volume to move outside of the space defined by the Planning Envelope Volume, shown by item 413.

The encapsulation metric employed to quantify the extent to which the Clinical Volume sits within the relevant Planning Envelope Volume is defined as follows: for one or more points on the Clinical Volume the shortest distance to the Planning Envelope Volume is determined. In an example of the invention if the point on the Clinical Volume is inside the Planning Envelope Volume then this distance is given a positive sign. If the point of the Clinical Volume is outside the Planning Envelope Volume then this distance is given a negative sign. The overall encapsulation metric is then the minimum value from the one or more signed shortest distances.

Figure 5A:
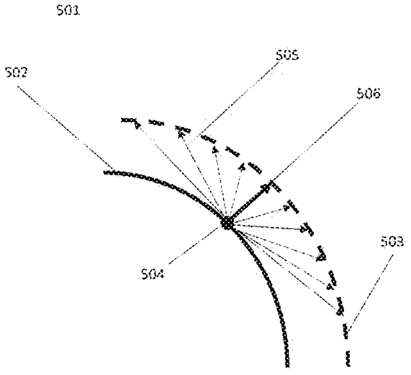
FIGS. 5(*a*), (*b*) and (*c*) show determination of a measurement metric according to the position of the clinical volume with respect to the position of the planning envelope volume.
Figure 5B:
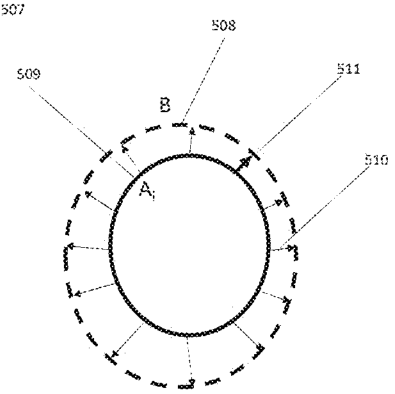
Figure 5C:
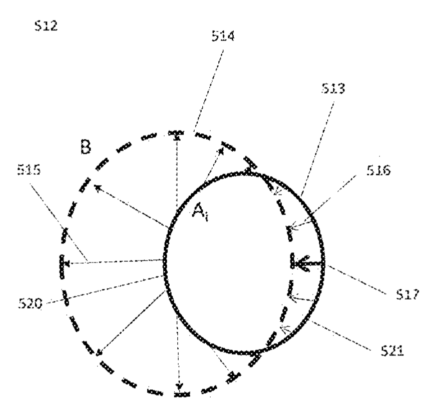

An example of the encapsulation metric is demonstrated in FIG. 5. FIG. 5(*a*) demonstrates a portion of a Clinical Volume, item 502, surrounded by a portion of Planning Envelope Volume, item 503. A representative point on the surface of the Clinical Volume is shown by item 504. A series of distances from the representative point on the Clinical Volume, 504, to the Planning Envelope Volume, 503, are shown as arrows of different length, items 505. The shortest distance from the representative point on the Clinical Volume, 504, to the Planning Envelope Volume, 503, is shown by the bold arrow, item 506.

FIG. 5(*b*), 507, demonstrates a case where the Clinical Volume, 509, is still entirely enclosed within the Planning Envelope Volume, 508. One or more representative points are designated on the surface of the clinical volume. For each of the one or more representative point on the Clinical Volume the shortest distance to the Planning Envelope Volume is determined, shown by the thin arrows, 510. In an example of the invention when the one or more representative points on the clinical volume are within the Planning Envelope Volume, the distance is classified as either a positive or negative internal distance, whereas when the one or more representative points on the Clinical Volume are external to the Planning envelope Volume the distance is an external distance classified with an opposite sign to the internal distance. An encapsulation metric value is determined as either: the minimum of the signed shortest distance value when the internal distance is classified as positive, or the maximum of the signed shorted distance when the internal distance is classified as negative, of the distances for the one or more representative points.

In this case as shown in FIG. 5(*b*), each distance from the Clinical Volume to the Planning Envelope Volume will have a positive value, as the Clinical Volume is fully enclosed by the Planning Envelope Volume. Of these the minimum value, which is the value that will be reported as the encapsulation metric, is shown by the thick arrow, 511. All of the other arrows in this figure have a larger length than the arrow indicated at 511.

FIG. 5(*c*), 512, demonstrates a case where a part of the Clinical Volume, 513, has moved beyond the Planning Envelope Volume, 514. In this example of the invention part of the Clinical Volume 520 is still within the Planning Envelope Volume, and part of the Clinical Volume 521 is now external to the Planning Envelope Volume. For each point on the Clinical Volume (both external to the Planning Envelope Volume and internal to the Planning Envelope Volume) the shortest distance to the Planning Envelope Volume is determined. For those points on the part of the Clinical Volume 520 that are still within the Planning Envelope Volume this distance is given a positive value, shown by the closed arrow heads, 515. For those points that are on region 521 of Clinical Volume that fall outside the Planning Envelope Volume, this distance is given a negative value, shown by the open arrow heads, 516. The reported encapsulation metric is the minimum of the signed shortest distances, as shown by the bold arrow, 517. In this case, in this example of the invention the encapsulation metric will also have a negative value as the shortest distance is between the PEV and a part of the CV that is external to the PEV.

In an example of the invention, after the planning envelope volume has been defined, a distance transform is calculated around the planning envelope volume and this is used to determine the encapsulation metric. Alternatively, the encapsulation metric is determined by simulation of translations of the one or more treatment clinical volumes relative to the planning envelope volume. In an embodiment of the invention the simulated translation is a linear translation.

Figures 6A, 6B:
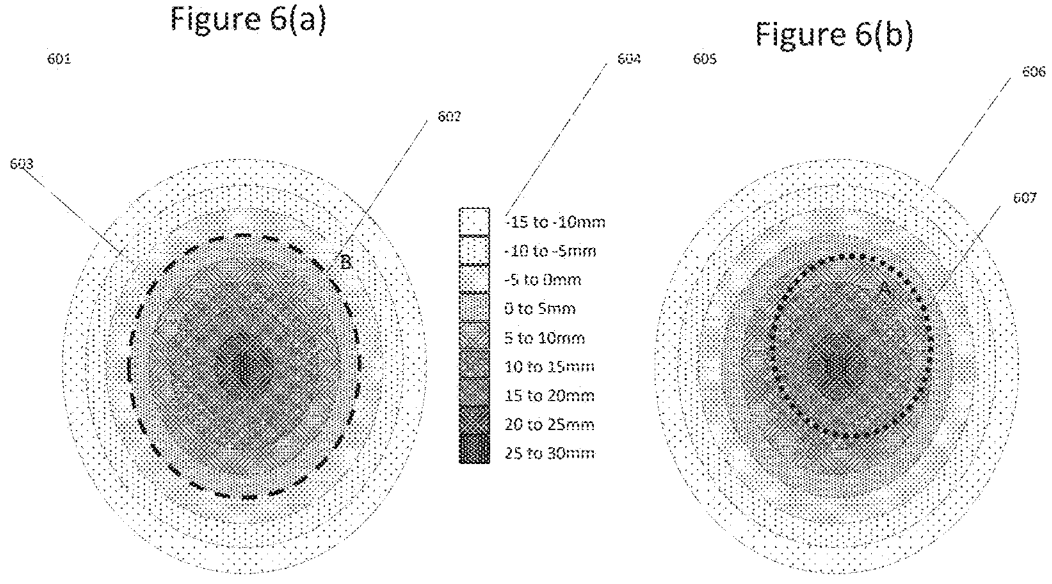
FIGS. 6(*a*)-(*c*) show a method to calculate the measurement metric according to an embodiment of the invention.
Figure 6C:
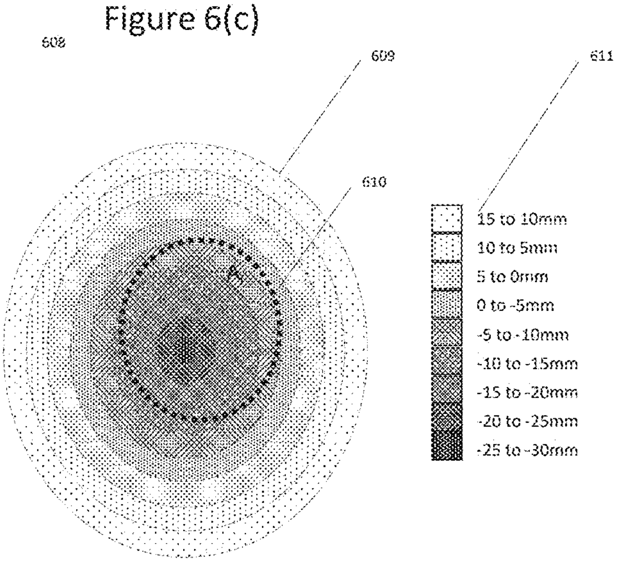
Figure 7:
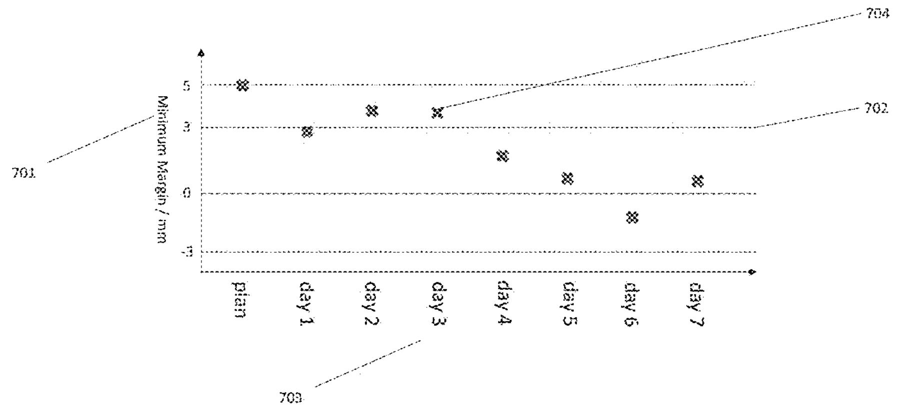
FIG. 7 is a plot of measurement metric against time for an embodiment of the invention.

One example of a method to efficiently calculate the encapsulation metric is shown in FIG. 6. FIG. 6(*a*) shows the calculation during the radiotherapy planning phase 601. Once the PEV, 602, (shown by the dashed line) has been determined a signed distance transform is calculated, 603, with legend 604. The signed distance transform will be a three dimensional matrix of signed distance values. In this example the matrix values are represented by a series of radial sections of 5 mm width. The section at the centre of the image is +25 to +30 mm from the PEV. This is surrounded by the +20-+25 mm radial section. The image has a series of concentric 5 mm sections, passing from +5 mm to 0 mm at the inner boundary of the PEV, 0 to −5 mm on the outside of the PEV, to −10 to −15 mm on the edge of the image, furthest away from the PEV.

The signed distance transform to determine the encapsulation metric can be computed by any method detailed in the scientific literature, such as the method by Borgefors [1]. This signed distance transform shows, for any point in the treatment co-ordinate system, the shortest distance from the clinical volume to the PEV. In an example of the invention the value is positive if the point is within the PEV (as shown in FIG. 5(*a*)) and the value is negative is the point is outside the PEV as shown in FIG. 5(*b*).

The radiotherapy treatment phase is shown in FIG. 6(*b*). The signed distance transform from the planning phase, 603, is copied directly into the treatment space, 606. That is the three dimensional matrix of signed distance values are mapped to the treatment space, represented in this diagram by a series of radial sections with signed distance values from 25 to 30 mm to −15 to −10 mm. The surface of the clinical volume 607 is shown, and in this example of the invention the Clinical volume is contained entirely within the Planning envelope volume so the encapsulation metric will have a positive value for this example of the invention. As shown, the Clinical Volume is offset to the upper right quadrant with respect to the origin of the original Planning Envelope Volume. Given this and the location of the Clinical Volume, 607, on the treatment image, the minimum of these signed shortest distance values on the boundary of Clinical Volume can be found by any means. One trivial method would be by exhaustive search along all boundary points of the Clinical Volume, but more efficient algorithms like priority queues or sorting algorithms are equally possible. Alternatively, a convention could be applied wither the distance transform is given positive values for parts of the CV that are outside the PEV and negative values for the parts of the CV on the inside of the PEV (a reversal of the convention used in FIG. 5). In this scenario the encapsulation measure would be the maximum of the signed shortest distance values on the boundary of the CV, rather than the minimum. This is shown in FIG. 6(*c*).

The encapsulation metric of this invention can be calculated using a 3D or 2D geometry. In the 3D case the encapsulation metric will be sensitive to volume changes that occur in any direction. An example of the use of the 3D case would be where the Clinical Volume being tracked is the target Clinical Target Volume and movement is any direction will be clinically significant. In the 2D case the encapsulation metric will not be sensitive to volume changes that occur in one image axis. An example of the use of the 2D case is where the spinal cord is the Clinical Volume being tracked, but it extends above and below the region of the treatment image. In this case it might be better if the encapsulation metric was not sensitive to changes in the cranio-caudal direction since those changes may not be clinically relevant. In the method described in FIG. 600 the difference between the 2D and 3D method is in the calculation of the signed distance transform, 603. To produce a 3D encapsulation metric the signed distance transform will describe the distance from the Clinical Volume to the Planning Envelope Volume in any direction. To produce a 2D encapsulation metric the signed distance transform will describe the distance from the Clinical Volume to the Planning Envelope Volume only in the 2D plane which is orthogonal to the direction being excluded. A further extension of the invention is to clip the region in which the metric is calculated to avoid areas likely to produce incorrect results, such as at the very top and bottom of the planning or treatment image sequence, or to remove areas distant from the treatment area.

An alternative but less efficient method to calculate the minimum margin encapsulation metric is to simulate a large number of linear translations of the treatment Clinical Volumes and identify the magnitude of linear translation required for each Clinical Volume to breach the associated Planning Envelope Volume.

In an example of the invention the planning envelope volume is defined as the clinical volume plus a margin specified by a predetermined protocol. Preferably, the clinical volume is a clinical target volume for treatment planning or gross tumour volume. Alternatively, the clinical volume represents an organ at risk to be avoided during treatment A key advantage of the minimum margin encapsulation metric over others that have been previously reported is that the encapsulation is signed so that movement of the Clinical Volume outside the Planning Envelope Volume (a negative value for the encapsulation metric) appears differently to movement of the Clinical Volume inside the Planning Envelope Volume (a positive value for the encapsulation metric). In an example of the invention the method also includes the step of displaying the one or more determined encapsulation metrics to a system user. The principle of displaying the encapsulation metric to the user can be extended to give greater insight and flexibility. A further embodiment of this invention uses the encapsulation metric for tracking patient changes. In an example of the invention the steps of the method may be repeated over a set time period to monitor changes in the encapsulation metric on the treatment images. Preferably, the set time period may vary between 1 day and 3 months. In some examples of the invention the changes in the encapsulation metric are displayed to the user. For this, a change tracking view is shown in FIG. 700, which plots the encapsulation metric, 701, preferably for each day of treatment, 703, although other time intervals may also be used. In this plot it is possible to display thresholds of concern, 702, where encapsulation metric values in excess of a pre-set threshold indicate unsafe amounts of movement of the subject in the scanner. The threshold value can either be a global value for each Planning Envelope Volume or an individual differing value for each Planning Envelope Volume. Each threshold value can be set in a multitude of ways: either as a user input value, as organ specific standard values, or algorithmically determined based on any combination of position, size, radiation dose tolerance or objectives, treatment technique and vicinity to other Clinical Volumes or Planning Envelope Volumes. In this example the points for this case, 704, show a downward trend with the Clinical Volume moving outside the Planning Envelope Volume on day 6 of treatment. Other implementations of a system utilising the encapsulation metric for change tracking could involve using the encapsulation metric as input into a decision support algorithm such as one which autonomously monitors the change in the encapsulation metric against statistical criteria and advises when a statistically significant change in behavior has occurred.

Figure 8A:
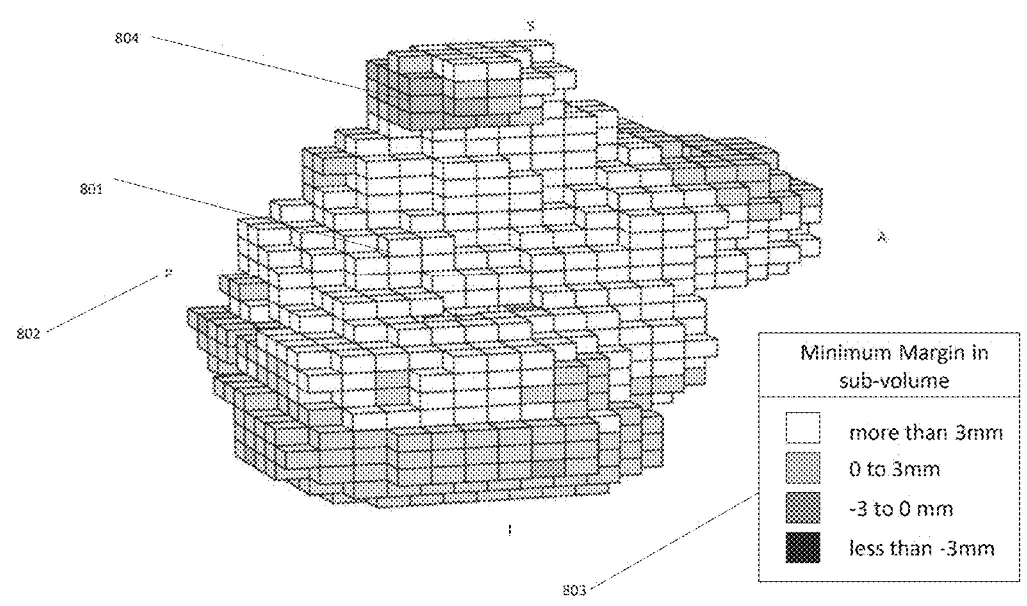
FIGS. 8(*a*) and 8(*b*) area rendered 3D views of a clinical volume in accordance with an embodiment of the invention.
Figure 8B:
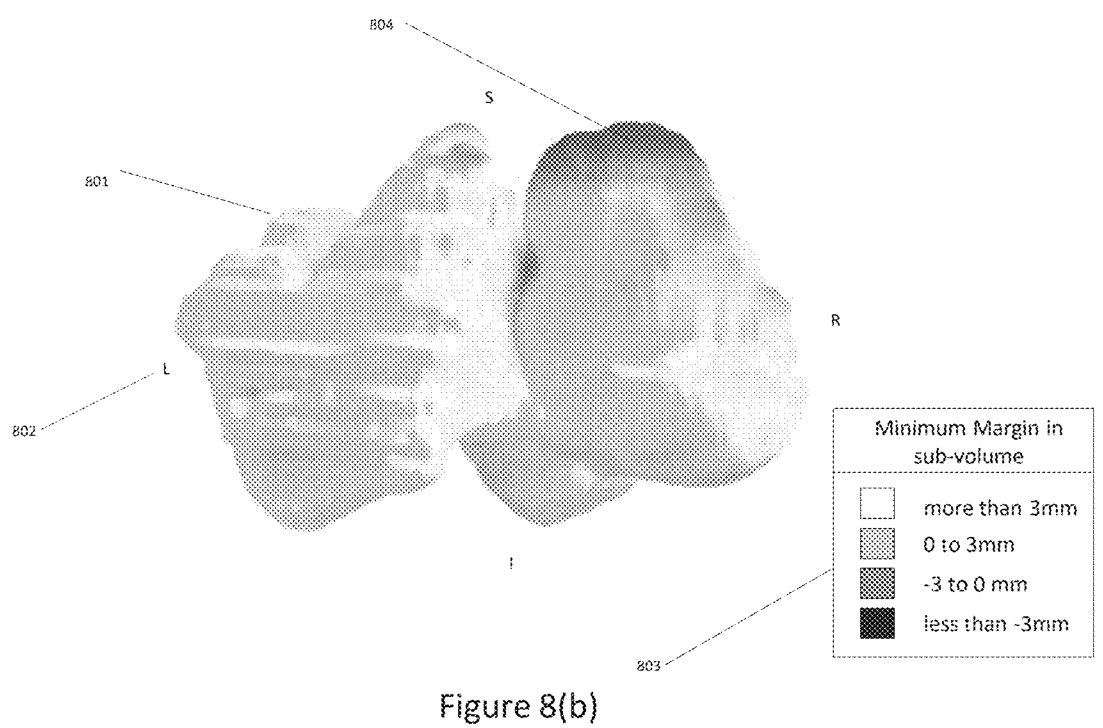
Figure 9:
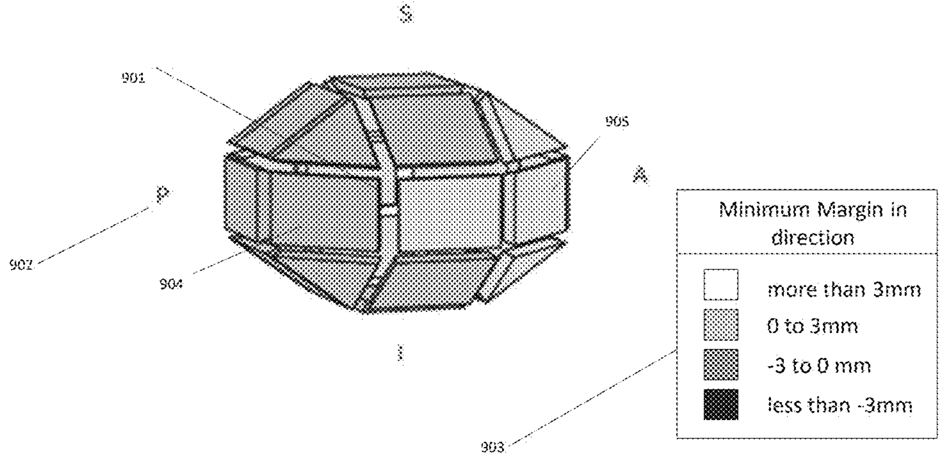
FIG. 9 is a 3D view of information related to the measurement metric for the clinical volume.

Whilst a global encapsulation metric is useful to assist immediate decision making and error tracking in an example of the invention other views may also assist users in understanding what is happening with the patient case. In a further embodiment of the invention, FIGS. 8(*a*) and 8(*b*) show two alternative 3D surface rendered views of a Clinical Volume, 801. In FIG. 8(*a*) each cube, 801, represents a portion of the Clinical Volume surface. The surface can be apportioned according to a grid or mesh, preferably set by the user or algorithmically based on any combination of patient geometry, surface curvature and dose grid or image parameters. In the case that the apportionment is sufficiently fine the surface may appear to the user as smooth and continuous (see FIG. 8(*b*). Orientation labels, 802, enable the user to relate the 3D rendered surface view to the patient anatomy. In this example of the invention, the encapsulation metric is determined using the minimum signed distance, however, it also applies for the encapsulation metric determined as the maximum distance as described above. The representation of each element of the surface is varied by means such as colour, transparency, texture or labels according to the shortest distance to the Planning Envelope Volume (or the maximum distance if the alternative method of calculating the metric is used) at that position on the Clinical Volume surface as indicated in the legend, 803. One example of this representation would be a heat map where low values of the metric are displayed hotter. The user can configure any other colour scheme they find more useful. This allows the user to quickly identify the region of greatest concern, 804. FIG. 8(*b*) shows a 3D surface image of the volume, rather than a cubed version.

The only tool the user has to immediately correct any patient position problem as highlighted by the determination of the encapsulation metric is to move the patient couch, which may only facilitate a linear translation. In an example of the invention the subject may be in a specified position in a scanner for the planning image and the treatment image, and the system user can adjust the subject position within the scanner according to the one or determined encapsulation metrics.

A further embodiment therefore calculates the minimum margin metric by direction and displays this information to the user. One method to achieve this would be to assign each point on the Clinical Volume surface to an orientation based on the 3D angle of the structure surface at this point. The 3D angle of the structure surface can be easily determined from the gradient of the signed distance transform, 603. Other standard methods exist within computer graphics to determine the 3D angle of orientation of a surface. The continuous 3D angle values for all points on the surface would then be binned into discrete orientations based on predetermined limits. In the calculation of the encapsulation metric the points on the CV surface falling into each orientation bin would be treated independently from each other, resulting in a separate encapsulation metric value for each orientation.

Another method to achieve the encapsulation metric by direction is by simulating a patient position shift in each direction and reporting the distance moved in each direction before the Clinical Volume breaches the Planning Envelope Volume. This would advise the user whether a couch move can be achieved in any direction without causing the Clinical Volume to move outside the Planning Envelope Volume. This directional minimum margin metric can be displayed to the user in many forms such as a simple table, using 2D or 3D directional arrows of length equal to the metric value, or using a 2D or 3D representation of the CV shape with indicators on the edges corresponding with each direction. An example on how to display this information is shown in FIG. 900. A 3D view is shown with indicators, 901, showing the minimum margin metric in each direction. The directions are provided by the orientation labels, 902. As before the colour of the indicator shows the minimum margin in each direction as described by the legend, 903. In this case the user sees that the margin metric is slightly worse in the posterior direction, 904, than in the anterior direction, 905, and the situation may be improved with a small anterior movement of the couch.

[1] Borgefors, On Digital Distance Transforms in Three Dimensions, Computer Vision and Image Understanding, 1996, 64 (3); 368-376

Other image guided interventional medical modalities involving the tracking of patient anatomy over time.

Examples of this invention may be applied to any or all of the following: Picture archiving and communication systems (PACS); Advanced visualisation workstations; Imaging Acquisition Workstations; Web-based or cloud-based medical information and image systems; Radiotherapy Treatment planning system (TPS); Radiotherapy linear accelerator consoles; Radiotherapy proton beam console.

The present invention has been described with reference to the accompanying drawings. However, it will be appreciated that the present invention is not limited to the specific examples herein described and as illustrated in the accompanying drawings. Furthermore, because the illustrated embodiments of the present invention may for the most part, be implemented using electronic components and circuits known to those skilled in the art, details will not be explained in any greater extent than that considered necessary as illustrated above, for the understanding and appreciation of the underlying concepts of the present invention and in order not to obfuscate or distract from the teachings of the present invention.

The invention may be implemented in a computer program for running on a computer system, at least including code portions for performing steps of a method according to the invention when run on a programmable apparatus, such as a computer system or enabling a programmable apparatus to perform functions of a device or system according to the invention.

A computer program is a list of instructions such as a particular application program and/or an operating system. The computer program may for instance include one or more of: a subroutine, a function, a procedure, an object method, an object implementation, an executable application, an applet, a servlet, a source code, an object code, a shared library/dynamic load library and/or other sequence of instructions designed for execution on a computer system. Therefore, some examples describe a non-transitory computer program product having executable program code stored therein for automated contouring of cone-beam CT images.

The computer program may be stored internally on a tangible and non-transitory computer readable storage medium or transmitted to the computer system via a computer readable transmission medium. All or some of the computer program may be provided on computer readable media permanently, removably or remotely coupled to an information processing system. The tangible and non-transitory computer readable media may include, for example and without limitation, any number of the following: magnetic storage media including disk and tape storage media; optical storage media such as compact disk media (e.g., CD ROM, CD R, etc.) and digital video disk storage media; non-volatile memory storage media including semiconductor-based memory units such as FLASH memory, EEPROM, EPROM, ROM; ferromagnetic digital memories; MRAM; volatile storage media including registers, buffers or caches, main memory, RAM, etc.

A computer process typically includes an executing (running) program or portion of a program, current program values and state information, and the resources used by the operating system to manage the execution of the process. An operating system (OS) is the software that manages the sharing of the resources of a computer and provides programmers with an interface used to access those resources. An operating system processes system data and user input, and responds by allocating and managing tasks and internal system resources as a service to users and programs of the system.

The computer system may for instance include at least one processing unit, associated memory and a number of input/output (I/O) devices. When executing the computer program, the computer system processes information according to the computer program and produces resultant output information via I/O devices.

In the foregoing specification, the invention has been described with reference to specific examples of embodiments of the invention. It will, however, be evident that various modifications and changes may be made therein without departing from the scope of the invention as set forth in the appended claims and that the claims are not limited to the specific examples described above.

Those skilled in the art will recognize that the boundaries between logic blocks are merely illustrative and that alternative embodiments may merge logic blocks or circuit elements or impose an alternate decomposition of functionality upon various logic blocks or circuit elements. Thus, it is to be understood that the architectures depicted herein are merely exemplary, and that in fact many other architectures can be implemented which achieve the same functionality.

Any arrangement of components to achieve the same functionality is effectively 'associated' such that the desired functionality is achieved. Hence, any two components herein combined to achieve a particular functionality can be seen as 'associated with' each other such that the desired functionality is achieved, irrespective of architectures or intermediary components. Likewise, any two components so associated can also be viewed as being 'operably connected,' or 'operably coupled,' to each other to achieve the desired functionality.

Furthermore, those skilled in the art will recognize that boundaries between the above described operations merely illustrative. The multiple operations may be combined into a single operation, a single operation may be distributed in additional operations and operations may be executed at least partially overlapping in time. Moreover, alternative embodiments may include multiple instances of a particular operation, and the order of operations may be altered in various other embodiments.

However, other modifications, variations and alternatives are also possible. The specifications and drawings are, accordingly, to be regarded in an illustrative rather than in a restrictive sense.

In the claims, any reference signs placed between parentheses shall not be construed as limiting the claim. The word 'comprising' does not exclude the presence of other elements or steps then those listed in a claim. Furthermore, the terms 'a' or 'an,' as used herein, are defined as one or more than one. Also, the use of introductory phrases such as 'at least one' and 'one or more' in the claims should not be construed to imply that the introduction of another claim element by the indefinite articles 'a' or 'an' limits any particular claim containing such introduced claim element to inventions containing only one such element, even when the same claim includes the introductory phrases 'one or more' or 'at least one' and indefinite articles such as 'a' or 'an.' The same holds true for the use of definite articles. Unless stated otherwise, terms such as 'first' and 'second' are used to arbitrarily distinguish between the elements such terms describe. Thus, these terms are not necessarily intended to indicate temporal or other prioritization of such elements. The mere fact that certain measures are recited in mutually different claims does not indicate that a combination of these measures cannot be used to advantage

What is claimed is:

1. A system for analyzing medical images to determine changes between a planning image and a treatment image of a subject, comprising:

a processor; and memory comprising instructions, which when executed by the processor cause the processor to:

receive a planning image of a subject and a treatment image of the subject;

determine a clinical volume from the planning image;

define a planning envelope volume around the clinical volume;

determine a location of the clinical volume and the planning envelopes volume on the treatment image; and determine an encapsulation metric for the treatment image, wherein the encapsulation metric defines the extent of encapsulation of the clinical volume on the treatment image within the planning envelope volume.

2. The system of claim 1, the instructions when executed further cause the processor to:

designate one or more representative points on the surface of the clinical volume; and determine the shortest distance between the one or more representative points on the surface of the clinical volume to the planning envelope volume, wherein the encapsulation metric for the treatment image is determined based in part on the shortest distance between the one or more representative points on the surface of the clinical volume to the planning envelope volume.

3. The system of claim 2, wherein when a representative point of the one or more representative points on the clinical volume is within the planning envelope volume the shortest distance associated with the representative point is a number greater than or equal to zero and when the representative point on the clinical volume is external to the planning envelope volume the shortest distance associated with the representative point is a number less than zero, and wherein a value of the encapsulation metric is either the minimum of the shortest distance when the number is greater than or equal to zero or the maximum of the of the shortest distance when the number is less than zero.

4. The system of claim 1, wherein the planning image and the treatment images are three-dimensional (3D) images.

5. The system of claim 1, wherein the planning image and/or the treatment image are computed tomography (CT) images, positron emission tomography (PET) images, single photon emission computed tomography (SPECT) images, or magnetic resonance imaging (MRI) images.

6. The system of claim 1, the instructions when executed further cause the processor to calculate a distance transform around the planning envelope volume, wherein the encapsulation metric is determined based in part on the distance transform.

7. The system of claim 1, the instructions when executed further cause the processor to determine the encapsulation metric based in part on a simulated translations of the clinical volumes on the treatment image relative to the planning envelope volume.

8. The system of claim 7, wherein the simulated translation is a linear translation.

9. The system of claim 1, wherein the planning envelope volume is defined as the clinical volume plus a margin specified by a predetermined protocol.

10. The system of claim 1, wherein the clinical volume is a clinical target volume for treatment planning or gross tumour volume.

11. The system of claim 1, wherein the clinical volume represents an organ at risk to be avoided in treatment.

12. A non-transitory computer readable medium comprising instruction that when executed by a processor of a treatment planning system cause the system to:

receive a planning image of a subject and a treatment image of the subject;

determine a clinical volume from the planning image;

define a planning envelope volume around the clinical volume;

determine a location of the clinical volume and the planning envelopes volume on the treatment image; and determine an encapsulation metric for the treatment image, wherein the encapsulation metric defines the extent of encapsulation of the clinical volume on the treatment image within the planning envelope volume.

13. The non-transitory computer readable medium of claim 12, the instruction, when executed by a processor of the treatment planning system further cause the system to:

determine a geometric relationship between the planning image and the treatment image;

identify one or more anatomical features on the treatment image; and determining the location of the clinical volumes on the treatment image based in part on mapping the clinical volume location to a location on the treatment image based on the geometric relationship and the one or more anatomical features.

14. The non-transitory computer readable medium of claim 12, the instruction, when executed by a processor of the treatment planning system further cause the system to repeatedly determine the encapsulation metric to monitor changes in the encapsulation metric over a period.

15. The non-transitory computer readable medium of claim 12, wherein the period is between 6 hours and 3 months.

16. The non-transitory computer readable medium of claim 12, the instruction, when executed by a processor of the treatment planning system further cause the system to display the encapsulation metric and the period on a display.

17. A computer-implemented method for analyzing medical images, comprising:

receiving, by a processor of an image planning system, a planning image of a subject and a treatment image of the subject;

determining, by the processor, a clinical volume from the planning image;

defining, by the processor, a planning envelope volume around the clinical volume;

determining, by the processor, a location of the clinical volume and the planning envelopes volume on the treatment image; and determining, by the processor, an encapsulation metric for the treatment image, wherein the encapsulation metric defines the extent of encapsulation of the clinical volume on the treatment image within the planning envelope volume.

18. The computer-implemented method of claim 17, further comprising:

generating a heat map representing the encapsulation metric; and displaying the heat map on a display.

19. The computer-implemented method of claim 17, further comprising:

designating one or more representative points on the surface of the clinical volume; and determining, by the processor, the shortest distance between the one or more representative points on the surface of the clinical volume to the planning envelope volume, wherein the encapsulation metric for the treatment image is determined based in part on the shortest distance between the one or more representative points on the surface of the clinical volume to the planning envelope volume.

20. The computer-implemented method of claim 17, further comprising:

determining, by the processor, the encapsulation metric based in part on a derived distance transform around the planning envelope volume; or determining the encapsulation metric based in part on a simulated translations of the clinical volumes on the treatment image relative to the planning envelope volume.

* * * * *